United States Patent
Chen et al.

(10) Patent No.: US 10,323,237 B2
(45) Date of Patent: Jun. 18, 2019

(54) LYSOZYME HAVING IMPROVED ENZYMATIC ACTIVITY

(71) Applicant: Chengdu Beacon Bio-Technology CO., Ltd., Chengdu (CN)

(72) Inventors: Chun-Chi Chen, Chengdu (CN); Tao Wang, Chengdu (CN); Jian-Wen Huang, Chengdu (CN); Rey-Ting Guo, Chengdu (CN)

(73) Assignee: CHENGDU BEACON BIO-TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 16/107,529

(22) Filed: Aug. 21, 2018

(65) Prior Publication Data

US 2019/0127716 A1    May 2, 2019

(30) Foreign Application Priority Data

Oct. 27, 2017   (CN) .......................... 2017 1 1026979

(51) Int. Cl.
| | | |
|---|---|---|
| *C12N 9/36* | (2006.01) | |
| *C12N 15/52* | (2006.01) | |
| *C12N 15/63* | (2006.01) | |

(52) U.S. Cl.
CPC ........... *C12N 9/2462* (2013.01); *C12N 15/52* (2013.01); *C12N 15/63* (2013.01); *C12Y 302/01017* (2013.01)

(58) Field of Classification Search
None
See application file for complete search history.

(56) References Cited

U.S. PATENT DOCUMENTS

2007/0207209 A1    9/2007  Murphy et al.

OTHER PUBLICATIONS

Wen Sai et al., "Advances in Research on Lysozyme and Strategies for New Antimicrobial Activity", China Biotechnology, 2015, 35 (8) : 116-125.
Hirakawa H et al., "Catalytic Reaction Mechanism of Goose Egg-white Lysozyme by Molecular Modelling of Enzyme-Substrate Complex", J. Biochem. 2008; 144 (6): 753-761.
UniProtKB—P84504 (Publication Date: Mar. 29, 2005).
Pooart J et al., "The Primary Structure of a Novel Goose-type Lysozyme from Rhea Egg White", Biosci. Biotechnol. Biochem., 68 (1), 159-169, 2004.

*Primary Examiner* — Kagnew H Gebreyesus
(74) *Attorney, Agent, or Firm* — Kirton McConkie; Evan R. Witt

(57) ABSTRACT

A lysozyme having improved enzymatic activity is disclosed. The amino acid sequence of the lysozyme is a modified amino acid sequence of SEQ ID NO: 2 or a modified amino acid sequence with at least 80% sequence identity of SEQ ID NO: 2, wherein the modification is a substitution of histidine at position 166 or a corresponding position with lysine.

6 Claims, 5 Drawing Sheets
Specification includes a Sequence Listing.

```
agaactaactgttacggagatgtttccagaattgatactactggagcttcatgtaagactgctaagcctgaaaagttgaactactgtgga
 R  T  N  C  Y  G  D  V  S  R  I  D  T  T  G  A  S  C  K  T  A  K  P  E  K  L  N  Y  C  G gttgctgctagtcgcaagattgctgaaagagatttgaggtcgatggatagatacaagactttgattaagaaggttggtcaaaagttgtgt
 V  A  A  S  R  K  I  A  E  R  D  L  R  S  M  D  R  Y  K  T  L  I  K  K  V  G  Q  K  L  C gttgaacctgctgttattgctggtattatttccagagaatcccatgctgggaaagcgttgaagaacggatggggcgacaacggtaacggt
 V  E  P  A  V  I  A  G  I  I  S  R  E  S  H  A  G  K  A  L  K  N  G  W  G  D  N  G  N  G tttggtttgatgcaagttgatagacggagccataagccagttggtgagtggaacggtgaaagacatttgattcaaggtactgaaattttg
 F  G  L  M  Q  V  D  R  R  S  H  K  P  V  G  E  W  N  G  E  R  H  L  I  Q  G  T  E  I  L atttctatgattaaggctatgcaagaaagtttcctagatggactaaggaacaacaattgaagggaggaatttccgcttacaacgctggt
 I  S  M  I  K  A  M  Q  R  K  F  P  R  W  T  K  Q  Q  L  K  G  G  I  S  A  Y  N  A  G ccaggtaacgttagaacttacgaacgcatggatattggtactactcatgatgattacgctaacgatgttgttgctagagcacaatactac
 P  G  N  V  R  T  Y  E  R  M  D  I  G  T  T  H  D  D  Y  A  N  D  V  V  A  R  A  Q  Y  Y aagcaacatggttactaa        - SEQ ID NO: 1
 K  Q  H  G  Y  *          - SEQ ID NO: 2
```

FIG. 2

| Primer | Primer Sequence |
|---|---|
| H166K | 5'- GGATATTGGTACTACTAAGGATGATTACGCTAACGAT -3' (SEQ ID NO: 3) |

FIG. 3 agaactaactgttacggagatgtttccagaattgatactactggagcttcatgtaagactgctaagcctgaaaagttgaactactgtgga
R T N C Y G D V S R I D T T G A S C R T A K F E K L N Y C G gttgctgctagtcgcaagattgctgaaagagatttgaggtcgatggatagatacaagactttgattaagaaggttggtcaaaagttgtgt
V A A S R K I A E R D L R S M D R Y K T L I K K V G Q K L C gttgaacctgctgttattgctggtattatttccagagaatcccatgctgggaaagcgttgaagaacggatggggcgacaacggtaacggt
V E P A V I A G I I S R E S R A G K A L E N G W G D N G N G tttggtttgatgcaagttgatagacggagccataagccagttggtgagtggaacggtgaaagacatttgattcaaggtactgaaattttg
F G L M Q V D R R S K P V G E W N G E R R L I Q G T E I L atttctatgattaaggctatgcaaagaaagtttcctagatggactaaggaacaacaattgaagggaggaatttccgcttacaacgctggt
I S M I K A M Q R K F P R W T K E Q Q L K G G I S A Y N A G ccaggtaacgttagaacttacgaacgcatggatattggtactact aaggatgattacgctaacgatgttgttgctagagcacaatactac
P G N V R T Y E R M D I G T T [K] D D Y A N D V V A R A Q Y Y aagcaacatggttactaa  - SEQ ID NO: 4
K Q H G Y *        - SEQ ID NO: 5

FIG. 4

SEQUENCE LISTING

```
<160> NUMBER OF SEQ ID NOS: 5

<210> SEQ ID NO 1
<211> LENGTH: 558
<212> TYPE: DNA
<213> ORGANISM: Rhea americana

<400> SEQUENCE: 1
agaactaact gttacggaga tgtttccaga attgatacta ctggagcttc atgtaagact      60
gctaagcctg aaaagttgaa ctactgtgga gttgctgcta gtcgcaagat tgctgaaaga     120
gatttgaggt cgatggatag atacaagact ttgattaaga aggttggtca aaagttgtgt     180
gttgaacctg ctgttattgc tggtattatt tccagagaat cccatgctgg gaaagcgttg     240
aagaacggat ggggcgacaa cggtaacggt tttggtttga tgcaagttga tagacggagc     300
```

```
cataagccag ttggtgagtg aacggtgaa agacatttga ttcaaggtac tgaaattttg    360
atttctatga ttaaggctat gcaaagaaag tttcctagat ggactaagga acaacaattg    420
aagggaggaa tttccgctta aacgctggt ccaggtaacg ttagaactta cgaacgcatg    480
gatattggta ctactcatga tgattacgct aacgatgttg ttgctagagc acaatactac    540
aagcaacatg gttactaa                                                  558
```

<210> SEQ ID NO 2
<211> LENGTH: 185
<212> TYPE: PRT
<213> ORGANISM: Rhea americana

<400> SEQUENCE: 2

```
Arg Thr Asn Cys Tyr Gly Asp Val Ser Arg Ile Asp Thr Thr Gly Ala
1               5                   10                  15

Ser Cys Lys Thr Ala Lys Pro Glu Lys Leu Asn Tyr Cys Gly Val Ala
            20                  25                  30

Ala Ser Arg Lys Ile Ala Glu Arg Asp Leu Arg Ser Met Asp Arg Tyr
        35                  40                  45

Lys Thr Leu Ile Lys Lys Val Gly Gln Lys Leu Cys Val Glu Pro Ala
    50                  55                  60

Val Ile Ala Gly Ile Ile Ser Arg Glu Ser His Ala Gly Lys Ala Leu
65                  70                  75                  80

Lys Asn Gly Trp Gly Asp Asn Gly Asn Gly Phe Gly Leu Met Gln Val
                85                  90                  95

Asp Arg Arg Ser His Lys Pro Val Gly Glu Trp Asn Gly Glu Arg His
            100                 105                 110

Leu Ile Gln Gly Thr Glu Ile Leu Ile Ser Met Ile Lys Ala Met Gln
        115                 120                 125

Arg Lys Phe Pro Arg Trp Thr Lys Glu Gln Gln Leu Lys Gly Gly Ile
    130                 135                 140

Ser Ala Tyr Asn Ala Gly Pro Gly Asn Val Arg Thr Tyr Glu Arg Met
145                 150                 155                 160

Asp Ile Gly Thr Thr His Asp Asp Tyr Ala Asn Asp Val Val Ala Arg
                165                 170                 175

Ala Gln Tyr Tyr Lys Gln His Gly Tyr
                180                 185
```

<210> SEQ ID NO 3
<211> LENGTH: 37
<212> TYPE: DNA
<213> ORGANISM: Artificial Sequence
<220> FEATURE:
<223> OTHER INFORMATION: Synthetically generated primer

<400> SEQUENCE: 3

```
ggatattggt actactaagg atgattacgc taacgat                              37
```

<210> SEQ ID NO 4
<211> LENGTH: 558
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 4

```
agaactaact gttacggaga tgtttccaga attgatacta ctggagcttc atgtaagact    60
```

```
gctaagcctg aaaagttgaa ctactgtgga gttgctgcta gtcgcaagat tgctgaaaga    120
gatttgaggt cgatggatag atacaagact ttgattaaga aggttggtca aaagttgtgt    180
gttgaacctg ctgttattgc tggtattatt tccagagaat cccatgctgg gaaagcgttg    240
aagaacggat ggggcgacaa cggtaacggt tttggtttga tgcaagttga tagacggagc    300
cataagccag ttggtgagtg aacggtgaaa agacatttga ttcaaggtac tgaaattttg    360
atttctatga ttaaggctat gcaaagaaag tttcctagat ggactaagga acaacaattg    420
aagggaggaa tttccgctta caacgctggt ccaggtaacg ttagaactta cgaacgcatg    480
gatattggta ctactaagga tgattacgct aacgatgttg ttgctagagc acaatactac    540
aagcaacatg gttactaa                                                  558
```

<210> SEQ ID NO 5
<211> LENGTH: 185
<212> TYPE: PRT
<213> ORGANISM: Artificial Sequence
<220> FEATURE:
<223> OTHER INFORMATION: Sequence synthetically translated from SEQ ID
      NO: 4

<400> SEQUENCE: 5

```
Arg Thr Asn Cys Tyr Gly Asp Val Ser Arg Ile Asp Thr Thr Gly Ala
1               5                   10                  15

Ser Cys Lys Thr Ala Lys Pro Glu Lys Leu Asn Tyr Cys Gly Val Ala
            20                  25                  30

Ala Ser Arg Lys Ile Ala Glu Arg Asp Leu Arg Ser Met Asp Arg Tyr
        35                  40                  45

Lys Thr Leu Ile Lys Lys Val Gly Gln Lys Leu Cys Val Glu Pro Ala
    50                  55                  60

Val Ile Ala Gly Ile Ile Ser Arg Glu Ser His Ala Gly Lys Ala Leu
65                  70                  75                  80

Lys Asn Gly Trp Gly Asp Asn Gly Asn Gly Phe Gly Leu Met Gln Val
                85                  90                  95

Asp Arg Arg Ser His Lys Pro Val Gly Glu Trp Asn Gly Glu Arg His
            100                 105                 110

Leu Ile Gln Gly Thr Glu Ile Leu Ile Ser Met Ile Lys Ala Met Gln
        115                 120                 125

Arg Lys Phe Pro Arg Trp Thr Lys Glu Gln Gln Leu Lys Gly Gly Ile
    130                 135                 140

Ser Ala Tyr Asn Ala Gly Pro Gly Asn Val Arg Thr Tyr Glu Arg Met
145                 150                 155                 160

Asp Ile Gly Thr Thr Lys Asp Asp Tyr Ala Asn Asp Val Val Ala Arg
                165                 170                 175

Ala Gln Tyr Tyr Lys Gln His Gly Tyr
                180                 185
```

LYSOZYME HAVING IMPROVED ENZYMATIC ACTIVITY

FIELD OF THE INVENTION

The present invention relates to a lysozyme, and more particularly to a lysozyme having improved enzymatic activity.

BACKGROUND OF THE INVENTION

Lysozyme (EC 3.2.1.17), also named muramidase, is a hydrolase acting on microbial cell walls, and is able to effectively hydrolyze the peptidoglycan of the bacterial cell wall by cleaving the β-1,4-glycosidic bond between the N-acetylmuramic acid and the N-acetylglucosamine of the peptidoglycan. Consequently, the cell wall is degraded due to the breakage of the peptidoglycan backbone, which results in lysis of the bacterial cell. The lysozyme is widely distributed in nature, such as in tears, saliva, snot and tissues of mammalians and in egg white of birds and poultries. Based on different resources, the lysozymes are divided into six types: chicken-type (c-type) lysozyme, goose-type (g-type) lysozyme, invertebrate-type (i-type) lysozyme, phage-type lysozyme, plant lysozyme and bacterial lysozyme. The lysozyme is a non-toxic protein and has no side effects to humans and mammalians. Due to the lytic property, the lysozyme is widely used in different industries these years. In dairy industry, the lysozyme can be used as a nature preservative; for example, adding lysozyme into the pasteurized milk can extend its shelf life. In food industry, adding lysozyme can extend the storage time of aquatic products and meat foods. In animal feed industry, adding lysozyme can improve animal production performance. According to studies, adding lysozyme into piglet diets can increase animal feed conversion, reduce diarrhea rates, improve piglet's health and reduce the use of antibiotics.

In recent years, due to global abuses of antibiotic drugs, more and more bacteria have developed into drug-resistant strains. Therefore, many countries start to prohibit the addition of antibiotics to livestock and poultry feeds, and scientists are trying hard to find solutions to replace traditional antibiotics, which draws more attention to lysozyme research. So far, many researches attempt to obtain lysozyme that can satisfy various industrial applications by either screening new genes from nature or modifying existing enzymes. In many strategies for modifying the enzyme, the rationale engineering that specifically mutates the enzyme gene based on the structural information of the enzyme protein is one of the major methods of modifying the enzyme. In this strategy, to improve the enzymatic activity is also a major focus of the industrial enzyme improvement. The improvement of the enzyme activity represents the reduction of the cost and the increase of the profit, and the enzyme having improved enzymatic activity is also beneficial to industrial applications.

Therefore, the present invention intends to improve the enzymatic activity of the lysozyme by rationale engineering, so as to further increase the industrial value of the lysozyme.

SUMMARY OF THE INVENTION

An object of the present invention is to modify a lysozyme by means of structural analysis and site-directed mutagenesis for effectively improving the enzymatic activity and further increasing the industrial value of the lysozyme.

According to an aspect of the present invention, there is provided a lysozyme comprising a modified amino acid sequence of SEQ ID NO: 2 or a modified amino acid sequence with at least 80% sequence identity of SEQ ID NO: 2, wherein the modification is a substitution of histidine at position 166 or a corresponding position with lysine.

In an embodiment, a gene encoding the amino acid sequence of SEQ ID NO: 2 is Rham gene isolated from an egg white of *Rhea Americana*.

In an embodiment, the lysozyme is a goose-type lysozyme.

In an embodiment, the lysozyme has a full length amino acid sequence of SEQ ID NO: 5.

According to another aspect of the present invention, there is provided a nucleic acid encoding the aforesaid lysozyme, and a recombinant plasmid comprising the aforesaid nucleic acid.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 2 shows the nucleotide sequence and the amino acid sequence of the wild-type lysozyme;
FIG. 3 shows the primer sequence for site-directed mutagenesis;
FIG. 4 shows the nucleotide sequence and the amino acid sequence of the mutant lysozyme H166K.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 1:
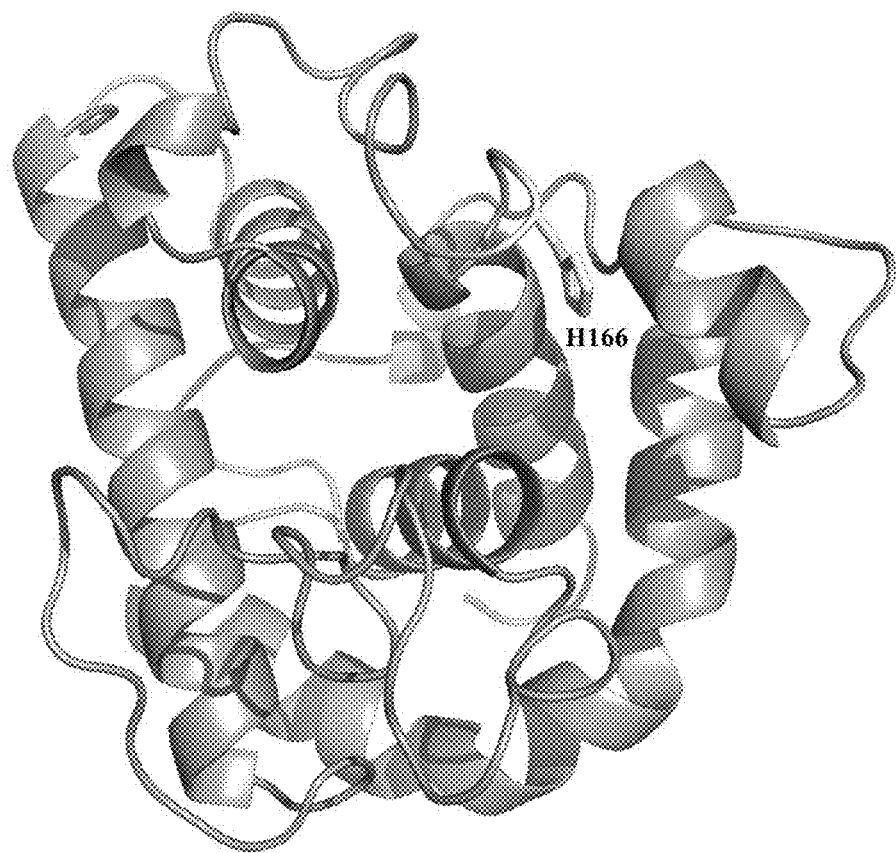
FIG. 1 shows the protein structure of the lysozyme Rham.

The lysozyme gene Rham used in the present invention is isolated from the egg white of *Rhea Americana*, and the encoded lysozyme belongs to goose-type (g-type) lysozyme and is a highly heat-resistant and acid-resistant protein. It is found recently that this lysozyme can be largely expressed in *Pichia pastoris*, which is commonly used in the industry, so it has potential industrial values. In order to further study and modify the lysozyme Rham, the present invention analyzed its protein structure and modified more than 40 amino acids which are located in the active region and have key features. FIG. 1 shows the protein structure of the lysozyme Rham. According to the alignment result from the superimposed protein structures, the histidine at position 166 (H166) was located in the active site and thus selected as one of the mutation sites for site-directed mutagenesis. It was found that the point mutation at H166 could improve the enzymatic activity of the lysozyme. Other mutations did not improve the enzymatic activity of the lysozyme and are not redundantly described here.

The enzyme modification processes and the resulted lysozyme protein are described in detail as follows.

FIG. 2 shows the nucleotide sequence and the amino acid sequence of the wild-type lysozyme. As shown in FIG. 2, the gene of the wild-type lysozyme Rham includes 558 base pairs (SEQ ID NO: 1, including the stop codon) and encodes 185 amino acids (SEQ ID NO: 2). First, the Rham gene was constructed into pPICZαA vector by EcoRI and NotI, and then the recombinant plasmids were transformed into competent cells to form wild-type expression vectors.

To improve the enzymatic activity of the lysozyme Rham, the present invention utilized site-directed mutagenesis and performed polymerase chain reaction (PCR) using the wild-type lysozyme gene as the template and using the primer shown in FIG. 3 for site-directed mutagenesis, wherein the primer sequence is numbered as SEQ ID NO: 3. The original template DNA was removed by DpnI. Then the recombinant plasmids were transformed into *E. coli* competent cells and selected by Zeocin. The mutated gene was further confirmed by DNA sequencing. Accordingly, the present invention constructed a mutant lysozyme H166K, wherein H166K means the histidine (H) at position 166 was substituted by lysine (K). FIG. 4 shows the nucleotide sequence and the amino acid sequence of the mutant lysozyme H166K, wherein the mutant lysozyme H166K gene also includes 558 base pairs (SEQ ID NO: 4, including the stop codon) and encodes 185 amino acids (SEQ ID NO: 5).

Then the recombinant gene was expressed in *Pichia pastoris*. The wild-type and the mutant lysozyme DNA plasmids were first linearized by PmeI and then transformed into *Pichia pastoris* by electroporation. The transformants were selected on YPD plates containing 100 μg/ml zeocin and cultured at 30° C. for 2 days. The selected colonies were inoculated in 5 ml of YPD at 30° C. and then amplified in 50 ml of BMGY at 30° C. for 24 hours. The cells were harvested and then resuspended in 20 ml of BMMY containing 0.5% methanol to induce protein expression at 30° C. for 4 days. The samples were collected at different time points for every 24 hours, and meanwhile, the methanol was added into the flask to the final concentration of 0.5%. The cells were harvested by centrifugation at 3500 rpm and the supernatant was collected for protein purification and activity determination.

The lysozyme activity was determined by the method modified from prior arts. The substrate used for the activity determination was *Micrococcus lysodeikticus* and the lysozyme activity was determined by turbidity method. First, a substrate solution of dried *Micrococcus lysodeikticus* in 66 mM potassium dihydrogen phosphate, pH 6.2, was prepared to a designated concentration ($A_{450}$=0.6-0.7). Then 0.1 ml of properly diluted lysozyme protein was added into 2.5 ml of the substrate solution and mixed quickly to detect the change of $OD_{450}$ in one minute at 25° C. One unit of the enzyme activity was defined as that amount of enzyme giving a decrease of 0.001 optical density units per min at 25° C.

Figure 5:
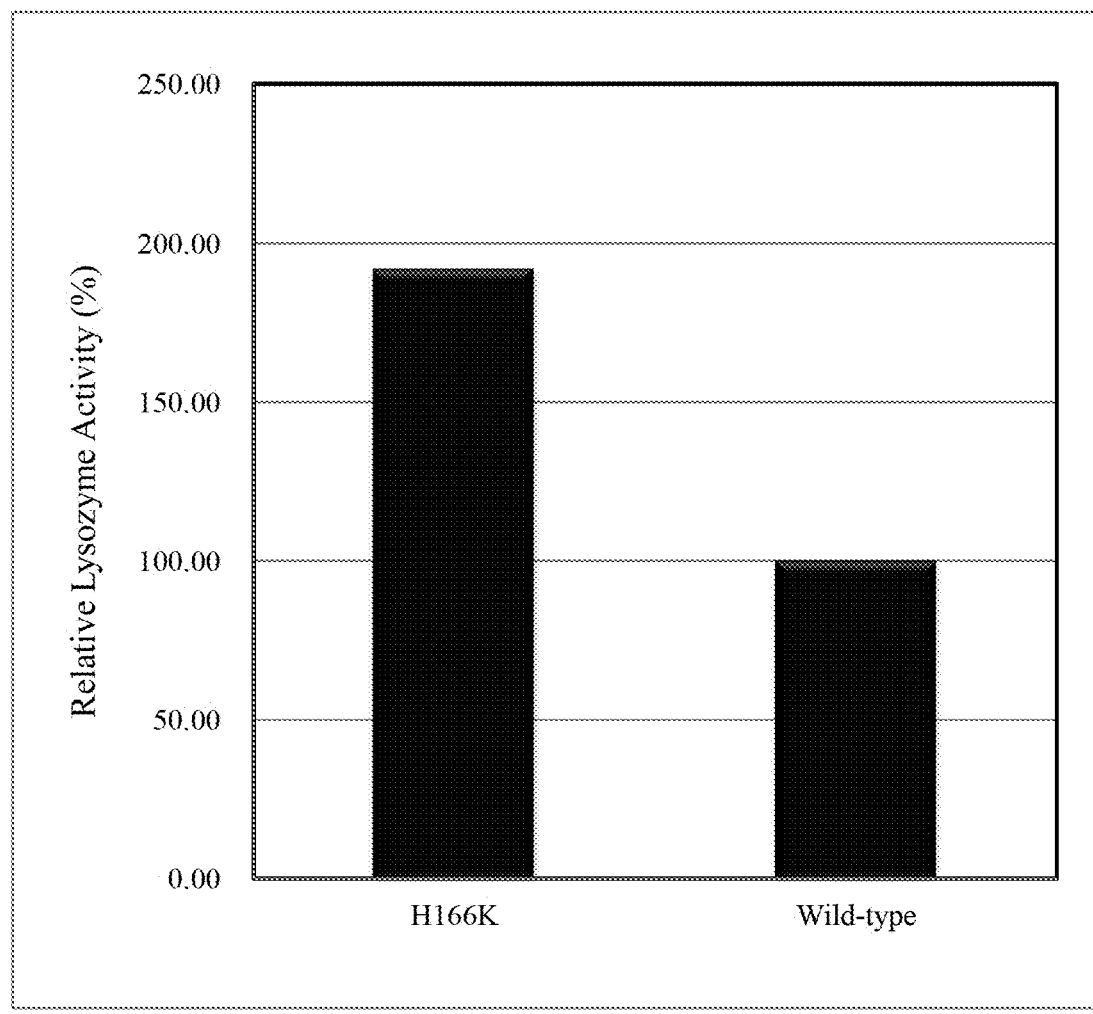
FIG. 5 shows the activity analysis of the wild-type lysozyme and the mutant lysozyme H166K.

FIG. 5 shows the activity analysis of the wild-type lysozyme and the mutant lysozyme H166K. As shown in FIG. 5, the specific activity of the mutant lysozyme H166K was 191% of the wild-type lysozyme, that means the activity of the mutant lysozyme H166K is much higher than that of the wild-type lysozyme. In addition, SOL fermentor was used to model the industrial large scale of enzyme production for the wild-type lysozyme and the mutant lysozyme H166K. The result showed that the activity of the mutant lysozyme H166K is also much higher than that of the wild-type lysozyme.

Besides, the enzymes usually have some variations among different species, but still have the same function, and most of them have at least 80% identity in amino acid sequence. Obviously, the enzymes are allowed to have some amino acid sequence variations but still maintain the enzyme function. In other words, the modified lysozyme sequence provided in the present invention is not limited to the sequence of SEQ ID NO: 2 having the substitution of histidine at position 166 with lysine, but also includes the sequence with at least 80% sequence identity of SEQ ID NO: 2 having the substitution of histidine at position 166 with lysine.

In conclusion, to increase the industrial value of the lysozyme Rham, the present invention chose the histidine at position 166 in the active site for further modification based on the structural analysis, and the histidine at position 166 was mutated to lysine by site-directed mutagenesis. According to the activity analysis, it is clear that the activity of the mutant lysozyme H166K is much higher than that of the wild-type lysozyme. Therefore, the Rham H166K mutant provided in the present invention has significantly improved lysozyme activity, so the production cost can be reduced and the industrial values are further increased.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A lysozyme comprising a modified amino acid sequence of SEQ ID NO: 2, wherein the modification is a substitution of histidine at position 166 with lysine.

2. The lysozyme according to claim 1 wherein a gene encoding the amino acid sequence of SEQ ID NO: 2 is Rham gene isolated from an egg white of *Rhea Americana*.

3. The lysozyme according to claim 1 being a goose-type lysozyme.

4. The lysozyme according to claim 1 having a full length amino acid sequence of SEQ ID NO: 5.

5. A nucleic acid encoding the lysozyme of claim 1.

6. A recombinant plasmid comprising the nucleic acid of claim 5.

* * * * *